United States Patent
Xu et al.

(10) Patent No.: US 11,091,757 B2
(45) Date of Patent: Aug. 17, 2021

(54) LACTOFERRIN APTAMERS AND USE THEREOF

(71) Applicant: NANJING UNIVERSITY, Nanjing (CN)

(72) Inventors: Danke Xu, Nanjing (CN); Hui Li, Nanjing (CN); Xiaohui Liu, Nanjing (CN); Zhu Chen, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 16/340,082

(22) PCT Filed: Feb. 7, 2017

(86) PCT No.: PCT/CN2017/073024
§ 371 (c)(1),
(2) Date: Apr. 5, 2019

(87) PCT Pub. No.: WO2018/068448
PCT Pub. Date: Apr. 19, 2018

(65) Prior Publication Data
US 2019/0270982 A1    Sep. 5, 2019

(30) Foreign Application Priority Data
Oct. 13, 2016  (CN) .......................... 201610894672.0

(51) Int. Cl.
| | | |
|---|---|---|
| *C12N 15/11* | (2006.01) | |
| *C12N 15/10* | (2006.01) | |
| *B01L 3/00* | (2006.01) | |
| *C12N 15/115* | (2010.01) | |
| *G01N 33/68* | (2006.01) | |

(52) U.S. Cl.
CPC .... *C12N 15/1048* (2013.01); *B01L 3/502707* (2013.01); *C12N 15/115* (2013.01); *G01N 33/68* (2013.01); *B01L 2200/16* (2013.01); *B01L 2300/0819* (2013.01); *B01L 2300/12* (2013.01); *C12N 2310/16* (2013.01); *G01N 2333/79* (2013.01)

(58) Field of Classification Search
CPC ... B01L 3/5027; C12Q 1/6825; C12Q 1/6874; C12Q 2563/143; C12Q 2525/205; C12Q 1/6806; C12Q 1/68; C12N 15/115; C12N 15/1048; C12N 2310/16
See application file for complete search history.

(56) References Cited

FOREIGN PATENT DOCUMENTS

CN        102703454 A    *  10/2012

OTHER PUBLICATIONS

Indyk et al., Determination of lactoferrin in bovine milk, colostrum and infant formulas by optical biosensor analysis, International Dairy Journal, vol. 15, pp. 429-438. (Year: 2005).*
Huang et al., Integrated microfluidic system for rapid screening of CRP aptamers utilizing systematic evolution of ligands by exponential enrichment (SELEX), Biosensors and Bioelectronics, vol. 25, pp. 1761-1766. (Year: 2010).*

* cited by examiner

*Primary Examiner* — Dana H Shin
(74) *Attorney, Agent, or Firm* — CBM Patent Consulting, LLC

(57) ABSTRACT

A method screens for aptamers by using a microarray microfluidic chip. The screening chip integrates microarray and microfluidic technology to integrate the positive and negative screening process on a microfluidic chip, and obtains aptamers with high affinity after 7 rounds of screening. It also discloses specific steps for screening of lactoferrin aptamers, including detailed processes such as chip preparation, positive and negative screening processes, and PCR amplification. The aptamers screened by the method have good specificity and affinity to the target protein. The aptamers are easier to be obtained than the antibody, and can be synthesized rapidly in large quantities in vitro. The preparation method is simpler and faster, so aptamers are expected to be a useful complement to antibody technology in many areas.

2 Claims, 5 Drawing Sheets
Specification includes a Sequence Listing.

SEQUENCE LISTING

<160> NUMBER OF SEQ ID NOS: 66

<210> SEQ ID NO 1
<211> LENGTH: 20
<212> TYPE: DNA
<213> ORGANISM: Artificial Sequence
<220> FEATURE:
<223> OTHER INFORMATION: Nucleotide sequence at the 5' end of a random
      base which is synthesized

<400> SEQUENCE: 1
gacaggcagg acaccgtaac                                           20

<210> SEQ ID NO 2
<211> LENGTH: 20
<212> TYPE: DNA
<213> ORGANISM: Artificial Sequence
<220> FEATURE:
<223> OTHER INFORMATION: Nucleotide sequence at the 3' end of a random
      base which is synthesized.

<400> SEQUENCE: 2
ctgctacctc cctcctcttc                                           20

<210> SEQ ID NO 3
<211> LENGTH: 20
<212> TYPE: DNA
<213> ORGANISM: Artificial Sequence
<220> FEATURE:
<223> OTHER INFORMATION: Forward primer that is synthesized

<400> SEQUENCE: 3
gacaggcagg acaccgtaac                                           20

<210> SEQ ID NO 4
<211> LENGTH: 20
<212> TYPE: DNA
<213> ORGANISM: Artificial Sequence
<220> FEATURE:
<223> OTHER INFORMATION: Backward primer that is synthesized.

<400> SEQUENCE: 4
gaagaggagg gaggtagcag                                           20

<210> SEQ ID NO 5
<211> LENGTH: 59
<212> TYPE: DNA
<213> ORGANISM: Artificial Sequence
<220> FEATURE:
<223> OTHER INFORMATION: AptamerN1 that is synthesized

<400> SEQUENCE: 5
gcaggacacc gtaaccctaa cacgtacggg gcatttatgg catagctctt cctccctgc      59

```
<210> SEQ ID NO 6
<211> LENGTH: 50
<212> TYPE: DNA
<213> ORGANISM: Artificial Sequence
<220> FEATURE:
<223> OTHER INFORMATION: AptamerN2 that is synthesized

<400> SEQUENCE: 6
aggcaggaca ccgtaaccgg tgcatctatg gctactagct tttcctgcct            50

<210> SEQ ID NO 7
<211> LENGTH: 59
<212> TYPE: DNA
<213> ORGANISM: Artificial Sequence
<220> FEATURE:
<223> OTHER INFORMATION: AptamerN3 that is synthesized

<400> SEQUENCE: 7
gcaggacacc gtaacgggca atcttgctct tattttcaca cttgataaat atgtcctgc   59

<210> SEQ ID NO 8
<211> LENGTH: 59
<212> TYPE: DNA
<213> ORGANISM: Artificial Sequence
<220> FEATURE:
<223> OTHER INFORMATION: AptamerN4 that is synthesized

<400> SEQUENCE: 8
gcaggacacc gtaacgggcg aacgctctaa ataaatggca tcaatttctt ttgccctgc   59

<210> SEQ ID NO 9
<211> LENGTH: 59
<212> TYPE: DNA
<213> ORGANISM: Artificial Sequence
<220> FEATURE:
<223> OTHER INFORMATION: AptamerN5 that is synthesized

<400> SEQUENCE: 9
gcaggacacc gtaacgggct tatgctctta aaaatcctga gcgactttt atgtactgc    59

<210> SEQ ID NO 10
<211> LENGTH: 59
<212> TYPE: DNA
<213> ORGANISM: Artificial Sequence
<220> FEATURE:
<223> OTHER INFORMATION: AptamerN6 that is synthesized

<400> SEQUENCE: 10
gcaggacacc gtaactcggg caaagctctg aataatgttc aaccaatatt ctgtcctgc   59

<210> SEQ ID NO 11
<211> LENGTH: 59
<212> TYPE: DNA
<213> ORGANISM: Artificial Sequence
<220> FEATURE:
<223> OTHER INFORMATION: AptamerN7 that is synthesized

<400> SEQUENCE: 11
gcaggacacc gtaacaatac tcctgttacc gtgcatctat ggccattggc ttttcctgc   59

<210> SEQ ID NO 12
<211> LENGTH: 59
<212> TYPE: DNA
<213> ORGANISM: Artificial Sequence
<220> FEATURE:
<223> OTHER INFORMATION: AptamerN8 that is synthesized
```

```
<400> SEQUENCE: 12
gcaggacacc gtaacacggg ctctgctttt ccaataatga caagtattgg atggcctgc      59

<210> SEQ ID NO 13
<211> LENGTH: 59
<212> TYPE: DNA
<213> ORGANISM: Artificial Sequence
<220> FEATURE:
<223> OTHER INFORMATION: AptamerN9 that is synthesized

<400> SEQUENCE: 13
gcaggacacc gtaacactct caaccatgac ggtgcaatat tggcgctagc tcttcctgc      59

<210> SEQ ID NO 14
<211> LENGTH: 59
<212> TYPE: DNA
<213> ORGANISM: Artificial Sequence
<220> FEATURE:
<223> OTHER INFORMATION: AptamerN10 that is synthesized

<400> SEQUENCE: 14
gcaggacacc gtaacgtatt aactagtacc agtgcatcta tggctattgc ttttcctgc      59

<210> SEQ ID NO 15
<211> LENGTH: 59
<212> TYPE: DNA
<213> ORGANISM: Artificial Sequence
<220> FEATURE:
<223> OTHER INFORMATION: AptamerN11 that is synthesized

<400> SEQUENCE: 15
gcaggacacc gtaacgttcg taacaacacg gcatctatgg ctttagctct tgtacctgc      59

<210> SEQ ID NO 16
<211> LENGTH: 52
<212> TYPE: DNA
<213> ORGANISM: Artificial Sequence
<220> FEATURE:
<223> OTHER INFORMATION: AptamerN12 that is synthesized

<400> SEQUENCE: 16
aggcaggaca ccgtaacacc ggtgcgtccc acggctccag ctcttcctgc ct             52

<210> SEQ ID NO 17
<211> LENGTH: 59
<212> TYPE: DNA
<213> ORGANISM: Artificial Sequence
<220> FEATURE:
<223> OTHER INFORMATION: AptamerN13 that is synthesized

<400> SEQUENCE: 17
gcaggacacc gtaacacggg ctgatgctct ctttatttta cctaaataaa gtgtcctgc      59

<210> SEQ ID NO 18
<211> LENGTH: 59
<212> TYPE: DNA
<213> ORGANISM: Artificial Sequence
<220> FEATURE:
<223> OTHER INFORMATION: AptamerN14 that is synthesized

<400> SEQUENCE: 18
gcaggacacc gtaacactgc tttatccccg tcggcttggc tcttcgacag tgtggctgc      59
```

```
<210> SEQ ID NO 19
<211> LENGTH: 40
<212> TYPE: DNA
<213> ORGANISM: Artificial Sequence
<220> FEATURE:
<223> OTHER INFORMATION: AptamerN15 that is synthesized

<400> SEQUENCE: 19
agcagacggg agacctttag agttgtaact tgagtctgct                         40

<210> SEQ ID NO 20
<211> LENGTH: 56
<212> TYPE: DNA
<213> ORGANISM: Artificial Sequence
<220> FEATURE:
<223> OTHER INFORMATION: AptamerN16 that is synthesized

<400> SEQUENCE: 20
ggcaggacac cgtaacccct agttcctggt gcatttatgg caaagctttt cctgcc       56

<210> SEQ ID NO 21
<211> LENGTH: 61
<212> TYPE: DNA
<213> ORGANISM: Artificial Sequence
<220> FEATURE:
<223> OTHER INFORMATION: AptamerN17 that is synthesized

<400> SEQUENCE: 21
caggcaggac accgtaaccg ggcatttgct ctcaatttag tctcaaattg tggcctgcct   60
g                                                                  61

<210> SEQ ID NO 22
<211> LENGTH: 50
<212> TYPE: DNA
<213> ORGANISM: Artificial Sequence
<220> FEATURE:
<223> OTHER INFORMATION: AptamerN18 that is synthesized

<400> SEQUENCE: 22
aggcaggaca ccgtaaccgg tgcatctatg gctactagct cttcctgcct              50

<210> SEQ ID NO 23
<211> LENGTH: 59
<212> TYPE: DNA
<213> ORGANISM: Artificial Sequence
<220> FEATURE:
<223> OTHER INFORMATION: AptamerN19 that is synthesized

<400> SEQUENCE: 23
gcaggacacc gtaacgggcg aacgctcttt attttggaac ccacaaaata atgttctgc    59

<210> SEQ ID NO 24
<211> LENGTH: 59
<212> TYPE: DNA
<213> ORGANISM: Artificial Sequence
<220> FEATURE:
<223> OTHER INFORMATION: AptamerN20 that is synthesized

<400> SEQUENCE: 24
gcaggacacc gtaacgggcg gagctcttcc atttcagatt tgtaaatgga tgtcactgc    59

<210> SEQ ID NO 25
<211> LENGTH: 59
<212> TYPE: DNA
<213> ORGANISM: Artificial Sequence
```

<220> FEATURE:
<223> OTHER INFORMATION: AptamerN21 that is synthesized

<400> SEQUENCE: 25
gcaggacacc gtaacgggct atgctctaaa ttcttcctac tgacgcaatt ttggactgc      59

<210> SEQ ID NO 26
<211> LENGTH: 59
<212> TYPE: DNA
<213> ORGANISM: Artificial Sequence
<220> FEATURE:
<223> OTHER INFORMATION: AptamerN22 that is synthesized

<400> SEQUENCE: 26
gcaggacacc gtaacgggtg cacactctta tttttacacg agccaaaaat atgtcctgc      59

<210> SEQ ID NO 27
<211> LENGTH: 61
<212> TYPE: DNA
<213> ORGANISM: Artificial Sequence
<220> FEATURE:
<223> OTHER INFORMATION: AptamerN23 that is synthesized

<400> SEQUENCE: 27
caggcaggac accgtaacgg tgcaattatt ggtgaacact cttccttagc ctgctactct     60
g                                                                    61

<210> SEQ ID NO 28
<211> LENGTH: 59
<212> TYPE: DNA
<213> ORGANISM: Artificial Sequence
<220> FEATURE:
<223> OTHER INFORMATION: AptamerN24 that is synthesized

<400> SEQUENCE: 28
gcaggacacc gtaactcatc ccaagctccg gtgccatcta tgggcttcgc ttttcctgc     59

<210> SEQ ID NO 29
<211> LENGTH: 52
<212> TYPE: DNA
<213> ORGANISM: Artificial Sequence
<220> FEATURE:
<223> OTHER INFORMATION: AptamerN25 that is synthesized

<400> SEQUENCE: 29
aggcaggaca ccgtaactga acggtcttgg ctactgcaca tttttcctgc ct           52

<210> SEQ ID NO 30
<211> LENGTH: 59
<212> TYPE: DNA
<213> ORGANISM: Artificial Sequence
<220> FEATURE:
<223> OTHER INFORMATION: AptamerN26 that is synthesized

<400> SEQUENCE: 30
gcaggacacc gtaacaacaa cttcgtatcc ggtgcattta tggcgaatgc ttttcctgc     59

<210> SEQ ID NO 31
<211> LENGTH: 59
<212> TYPE: DNA
<213> ORGANISM: Artificial Sequence
<220> FEATURE:
<223> OTHER INFORMATION: AptamerN27 that is synthesized

<400> SEQUENCE: 31
gcaggacacc gtaacactac cttctttcgg tgcgatccat tcggctttgc ttttcctgc      59

<210> SEQ ID NO 32
<211> LENGTH: 59
<212> TYPE: DNA
<213> ORGANISM: Artificial Sequence
<220> FEATURE:
<223> OTHER INFORMATION: AptamerN28 that is synthesized

<400> SEQUENCE: 32
gcaggacacc gtaacactgc tttatccccg tcggcttggc tcttcgacag tgttgctgc      59

<210> SEQ ID NO 33
<211> LENGTH: 59
<212> TYPE: DNA
<213> ORGANISM: Artificial Sequence
<220> FEATURE:
<223> OTHER INFORMATION: AptamerN29 that is synthesized

<400> SEQUENCE: 33
gcaggacacc gtaacactgc tttatccccg tcggcttgtc tcttcgacag tgtggctgc      59

<210> SEQ ID NO 34
<211> LENGTH: 40
<212> TYPE: DNA
<213> ORGANISM: Artificial Sequence
<220> FEATURE:
<223> OTHER INFORMATION: AptamerN30 that is synthesized

<400> SEQUENCE: 34
agcagacggg agacttttag agttgtaact tgagtctgct                           40

<210> SEQ ID NO 35
<211> LENGTH: 56
<212> TYPE: DNA
<213> ORGANISM: Artificial Sequence
<220> FEATURE:
<223> OTHER INFORMATION: AptamerN31 that is synthesized

<400> SEQUENCE: 35
ggcaggacac cgtaaccagt ataggtgcat ttttggcgca agctcttcct gccctg         56

<210> SEQ ID NO 36
<211> LENGTH: 56
<212> TYPE: DNA
<213> ORGANISM: Artificial Sequence
<220> FEATURE:
<223> OTHER INFORMATION: AptamerN32 that is synthesized

<400> SEQUENCE: 36
ggcaggacac cgtaaccatc gacggtgccg gtctcgggca ttttgctctt cctgcc         56

<210> SEQ ID NO 37
<211> LENGTH: 55
<212> TYPE: DNA
<213> ORGANISM: Artificial Sequence
<220> FEATURE:
<223> OTHER INFORMATION: AptamerN33 that is synthesized

<400> SEQUENCE: 37
ggcaggacac cgtaacccca ctcgaggtgc aattttggcg tgagctcttc ctgcc          55

<210> SEQ ID NO 38
<211> LENGTH: 56
<212> TYPE: DNA
<213> ORGANISM: Artificial Sequence
<220> FEATURE:
<223> OTHER INFORMATION: AptamerN34 that is synthesized

<400> SEQUENCE: 38
ggcaggacac cgtaacccct agttcctggt gcatctatgg caaagctctt cctgcc      56

<210> SEQ ID NO 39
<211> LENGTH: 56
<212> TYPE: DNA
<213> ORGANISM: Artificial Sequence
<220> FEATURE:
<223> OTHER INFORMATION: AptamerN35 that is synthesized

<400> SEQUENCE: 39
ggcaggacac cgtaacccct agttcctggt gcatttatgg caaagctctt cctgcc      56

<210> SEQ ID NO 40
<211> LENGTH: 56
<212> TYPE: DNA
<213> ORGANISM: Artificial Sequence
<220> FEATURE:
<223> OTHER INFORMATION: Aptamer36 that is synthesized

<400> SEQUENCE: 40
aggcaggaca ccgtaaccta caacggtgcc atctatgggc tttgcttttc ctgcct      56

<210> SEQ ID NO 41
<211> LENGTH: 56
<212> TYPE: DNA
<213> ORGANISM: Artificial Sequence
<220> FEATURE:
<223> OTHER INFORMATION: Aptamer37 that is synthesized

<400> SEQUENCE: 41
gacaggcagg acaccgtaac ggtgcatcca tggcttttag ctcttcctga actgtc      56

<210> SEQ ID NO 42
<211> LENGTH: 70
<212> TYPE: DNA
<213> ORGANISM: Artificial Sequence
<220> FEATURE:
<223> OTHER INFORMATION: Aptamer38 that is synthesized

<400> SEQUENCE: 42
aggcaggaca ccgtaacggt gcatctatgg ctttgctctt cctacctgtt ctacgagctg      60
ctacctccct      70

<210> SEQ ID NO 43
<211> LENGTH: 49
<212> TYPE: DNA
<213> ORGANISM: Artificial Sequence
<220> FEATURE:
<223> OTHER INFORMATION: Aptamer39 that is synthesized

<400> SEQUENCE: 43
aggcaggaca ccgtaacggt gcgtgtacac ggctctgctt ttcctgcct      49

<210> SEQ ID NO 44
<211> LENGTH: 82
<212> TYPE: DNA
<213> ORGANISM: Artificial Sequence
<220> FEATURE:
<223> OTHER INFORMATION: AptamerN40 that is synthesized

<400> SEQUENCE: 44
tgacaggcag gacaccgtaa caacaactcg atactggtgc cattttgggc gaacgctttt        60
cctgctacct ccctcctctt ca        82

<210> SEQ ID NO 45
<211> LENGTH: 82
<212> TYPE: DNA
<213> ORGANISM: Artificial Sequence
<220> FEATURE:
<223> OTHER INFORMATION: AptamerN41 that is synthesized

<400> SEQUENCE: 45
tgacaggcag gacaccgtaa caaccaacct acggtgcaat atttggcgga ttaagctctt        60
cctgctacct ccctcctctt ca        82

<210> SEQ ID NO 46
<211> LENGTH: 82
<212> TYPE: DNA
<213> ORGANISM: Artificial Sequence
<220> FEATURE:
<223> OTHER INFORMATION: AptamerN42 that is synthesized

<400> SEQUENCE: 46
tgacaggcag gacaccgtaa cacacgttaa cttacggcgc atttttttggc ttcagctctt        60 cctgctacct ccctcctctt ca        82

<210> SEQ ID NO 47
<211> LENGTH: 82
<212> TYPE: DNA
<213> ORGANISM: Artificial Sequence
<220> FEATURE:
<223> OTHER INFORMATION: AptamerN43 that is synthesized

<400> SEQUENCE: 47
tgacaggcag gacaccgtaa cacggtgcaa actcttggcg aatgcttttc ctgacccgct        60
actgctacct ccctcctctt ca        82

<210> SEQ ID NO 48
<211> LENGTH: 82
<212> TYPE: DNA
<213> ORGANISM: Artificial Sequence
<220> FEATURE:
<223> OTHER INFORMATION: AptamerN44 that is synthesized

<400> SEQUENCE: 48
tgacaggcag gacaccgtaa catacgattc tctcgcacat tgtggctccg cttttatgtt        60
actgctacct ccctcctctt ca        82

<210> SEQ ID NO 49
<211> LENGTH: 82
<212> TYPE: DNA
<213> ORGANISM: Artificial Sequence
<220> FEATURE:
<223> OTHER INFORMATION: AptamerN45 that is synthesized

<400> SEQUENCE: 49
tgacaggcag gacaccgtaa ccatacttcg gtgcatccca tggcgaattc gctcttcctt        60
cctgctacct ccctcctctt ca        82

```
<210> SEQ ID NO 50
<211> LENGTH: 82
<212> TYPE: DNA
<213> ORGANISM: Artificial Sequence
<220> FEATURE:
<223> OTHER INFORMATION: AptamerN46 that is synthesized

<400> SEQUENCE: 50
tgacaggcag gacaccgtaa ccgggcggag ctcttattac atcaactcgc tgtaatatgg      60
cctgctacct ccctcctctt ca                                              82

<210> SEQ ID NO 51
<211> LENGTH: 82
<212> TYPE: DNA
<213> ORGANISM: Artificial Sequence
<220> FEATURE:
<223> OTHER INFORMATION: AptamerN47 that is synthesized

<400> SEQUENCE: 51
tgacaggcag gacaccgtaa cgggcaatct tgctcttatt ttcacacctg ataaatatgt      60
cctgctacct ccctcctctt ca                                              82

<210> SEQ ID NO 52
<211> LENGTH: 82
<212> TYPE: DNA
<213> ORGANISM: Artificial Sequence
<220> FEATURE:
<223> OTHER INFORMATION: AptamerN48 that is synthesized

<400> SEQUENCE: 52
tgacaggcag gacaccgtaa cgggcttagc tctaaatcaa atcctcctta ttgattttgt      60
cctgctacct ccctcctctt ca                                              82

<210> SEQ ID NO 53
<211> LENGTH: 82
<212> TYPE: DNA
<213> ORGANISM: Artificial Sequence
<220> FEATURE:
<223> OTHER INFORMATION: AptamerN49 that is synthesized

<400> SEQUENCE: 53
tgacaggcag gacaccgtaa cgggtaacac tctacttata ccttgctata agttgtccgc      60
actgctacct ccctcctctt ca                                              82

<210> SEQ ID NO 54
<211> LENGTH: 82
<212> TYPE: DNA
<213> ORGANISM: Artificial Sequence
<220> FEATURE:
<223> OTHER INFORMATION: AptamerN50 that is synthesized

<400> SEQUENCE: 54
tgacaggcag gacaccgtaa cgggtttaac tctcaaatta gctctgcact acatttgtgc      60
cctgctacct ccctcctctt ca                                              82

<210> SEQ ID NO 55
<211> LENGTH: 82
<212> TYPE: DNA
<213> ORGANISM: Artificial Sequence
<220> FEATURE:
<223> OTHER INFORMATION: AptamerN51 that is synthesized
```

<400> SEQUENCE: 55
tgacaggcag gacaccgtaa cgtaactacg gacggcatct atggctatgc tcttgtccct    60
gctgctacct ccctcctctt ca    82

<210> SEQ ID NO 56
<211> LENGTH: 82
<212> TYPE: DNA
<213> ORGANISM: Artificial Sequence
<220> FEATURE:
<223> OTHER INFORMATION: AptamerN52 that is synthesized

<400> SEQUENCE: 56
tgacaggcag gacaccgtaa ctacctcttc catatcggtg caacatttgg cttagctctt    60
cctgctacct ccctcctctt ca    82

<210> SEQ ID NO 57
<211> LENGTH: 82
<212> TYPE: DNA
<213> ORGANISM: Artificial Sequence
<220> FEATURE:
<223> OTHER INFORMATION: AptamerN53 that is synthesized

<400> SEQUENCE: 57
tgacaggcag gacaccgtaa cttctgataa tcggtgcatc tatggcgtag ctcttcctca    60
cctgctacct ccctcctctt ca    82

<210> SEQ ID NO 58
<211> LENGTH: 82
<212> TYPE: DNA
<213> ORGANISM: Artificial Sequence
<220> FEATURE:
<223> OTHER INFORMATION: AptamerN54 that is synthesized

<400> SEQUENCE: 58
tgacaggcag gacaccgtaa cacggggcaa ttttggtgaa gctcttcctg cccagcctac    60
tctgctacct ccctcctctt ca    82

<210> SEQ ID NO 59
<211> LENGTH: 82
<212> TYPE: DNA
<213> ORGANISM: Artificial Sequence
<220> FEATURE:
<223> OTHER INFORMATION: AptamerN55 that is synthesized

<400> SEQUENCE: 59
tgacaggcag gacaccgtaa ccgggctatt gctctcaaac ttacacttta acgtttgggt    60
cctgctacct ccctcctctt ca    82

<210> SEQ ID NO 60
<211> LENGTH: 82
<212> TYPE: DNA
<213> ORGANISM: Artificial Sequence
<220> FEATURE:
<223> OTHER INFORMATION: AptamerN56 that is synthesized

<400> SEQUENCE: 60
tgacaggcag gacaccgtaa cgcgggcgaa gctcttaata cctctctatt atgtcctgtt    60
cctgctacct ccctccccTT ca    82

```
<210> SEQ ID NO 61
<211> LENGTH: 82
<212> TYPE: DNA
<213> ORGANISM: Artificial Sequence
<220> FEATURE:
<223> OTHER INFORMATION: AptamerN57 that is synthesized

<400> SEQUENCE: 61
tgacaggcag gacaccgtaa cgggcgaatg ctctctttgt tttatatata acaaagtgtc     60
tctgctacct ccctcctctt ca                                             82

<210> SEQ ID NO 62
<211> LENGTH: 82
<212> TYPE: DNA
<213> ORGANISM: Artificial Sequence
<220> FEATURE:
<223> OTHER INFORMATION: AptamerN58 that is synthesized

<400> SEQUENCE: 62
tgacaggcag gacaccgtaa cgggctctgc tctaaatttc gcccttgcac gaaattttgt     60
cctgctacct cccccctctt ca                                             82

<210> SEQ ID NO 63
<211> LENGTH: 82
<212> TYPE: DNA
<213> ORGANISM: Artificial Sequence
<220> FEATURE:
<223> OTHER INFORMATION: AptamerN59 that is synthesized

<400> SEQUENCE: 63
tgacaggcag gacaccgtaa cgggcttatg ctcttaaaaa tcctgagcga cttttatgt     60 actgctacct ccctcctctt ca                                             82

<210> SEQ ID NO 64
<211> LENGTH: 82
<212> TYPE: DNA
<213> ORGANISM: Artificial Sequence
<220> FEATURE:
<223> OTHER INFORMATION: AptamerN60 that is synthesized

<400> SEQUENCE: 64
tgacaggcag gacaccgtaa cggtgcggtc atatccggct ttgcttttcc tgccttctct    60
cctgctacct ccctcctctt ca                                             82

<210> SEQ ID NO 65
<211> LENGTH: 82
<212> TYPE: DNA
<213> ORGANISM: Artificial Sequence
<220> FEATURE:
<223> OTHER INFORMATION: AptamerN61 that is synthesized

<400> SEQUENCE: 65
tgacaggcgg gacaccgtaa ccccaacacg tacggggcat ttatggcata gctcttcctc    60
cctgctacct ccctcctctt ca                                             82

<210> SEQ ID NO 66
<211> LENGTH: 80
<212> TYPE: DNA
<213> ORGANISM: Artificial Sequence
<220> FEATURE:
<223> OTHER INFORMATION: Library is synthesized
```

```
<220> FEATURE:
<221> NAME/KEY: misc_feature
<222> LOCATION: (21)..(60)
<223> OTHER INFORMATION: n is a, c, g, or t

<400> SEQUENCE: 66
gacaggcagg acaccgtaac nnnnnnnnnn nnnnnnnnnn nnnnnnnnnn nnnnnnnnnn      60
ctgctacctc cctcctcttc                                                  80
```

LACTOFERRIN APTAMERS AND USE THEREOF

TECHNICAL FIELD

The invention belongs to the technical field of biological detection, and particularly relates to a method for screening aptamers by using a microarray microfluidic chip.

BACKGROUND TECHNIQUE

The aptamer has similar properties to the antibody, but it also exhibits superior characteristics to the antibody in many respects. (1) Aptamers are more specific with higher affinity for the target molecule than the antibody. (2) Aptamers are easier to obtain than antibodies (synthetically, independent of animals and cells), and can be synthesized quickly in vitro with large quantities, making preparation methods simpler and faster. (3) Different types of target molecules can be screened, including bio-toxic and semi-antigenic molecules, broadening the scope of application. (4) Aptamers are non-immunogenic and can be used repeatedly in the body. (5) Aptamers' stability is better than antibodies and conducive to storage. With the advancement of aptamer technology, aptamers will likely be a useful complement to antibody technology in many fields. Based on various advantages of aptamers, they have shown broad application prospects in analysis, clinical, environment, molecular recognition and drug screening.

At present, nanomaterial-based aptamer screening technology can eliminate the immobilization of proteins on the surface of solid phase substrates, which can effectively reduce the number of screening rounds and speed up the screening process. At the same time, the method based on microfluidic technology to improve the screening effect has been extensively studied. These methods include: capillary electrophoresis microfluidic aptamer screening, sol-gel microfluidic aptamer screening, surface plasmon resonance (SPR) microfluidic aptamer screening, magnetic bead microfluidic screening, and microfluidic screening techniques based on microspheres of various materials. In order to improve the efficiency of PCR amplification, scientists use agarose droplet PCR amplification technology and poly-emulsion PCR amplification (ePCR) technology, which can directly select positive clones for sequencing, avoiding the cumbersome process of cloning and sequencing in the traditional aptamer screening process. The above methods are intended to make the screening of aptamers more time-saving, automated, efficient and less expensive. Our job is to develop a new aptamer screening technique that is more stable, the screening process is repeatable, and the screening steps are quantifiable. The method optimizes the process of aptamer screening to make the process more simple and standardized.

SUMMARY OF THE INVENTION

The technical problem to be solved by the present invention is to provide a novel microarray microfluidic chip for applying to an aptamer screening method.

In order to solve the above technical problems, the technical solution adopted by the present invention is as follows:

A method for screening aptamers by using a microarray microfluidic chip, the microarray microfluidic chip is prepared as follows:

The PDMS pre-polymer and the curing agent are mixed at a mass ratio of 5:1 to 100:1. After being uniformly mixed, they are placed in a vacuum desiccator which is connected to a circulating water vacuum pump. The mixture are vacuumed for 30 min to remove bubbles, and then are poured on the microfluidic channel template. After curing, PDMS microfluidic channel is obtained. Lactoferrin and negative protein microarray with concentration of 0.1-10 mg/mL are prepared on the glass substrate. Then, the glass substrate and PDMS microfluidic channel are simultaneously plasma-treated, and closely adhered to obtain a microarray microfluidic chip.

The method for screening an aptamer using a microarray microfluidic chip according to claim 1, comprising the steps of:

(1) Screening preparation: The microarray microfluidic chip is incubated at a constant temperature for 1-12 h at 25-40° C. 5-20 mg/ml of BSA and 0.01-0.5 mM of random sequence short-chain ssDNA (20 nt) are added at 25-40° C. for 1-3 h, then the positive and negative channel on chip are cleaned by 150 µL of 1×PBST solution;

(2) The first round of screening: 0.1-10 nmol, 125 µL of the original library are heated at 95° C. for 3-15 min, and immediately frozen on ice for 10 s-5 min. The library are transferred at a flow rate of 1-5 µL/min by syringe pump into the positive channel, reacting at 25-40° C. for 30-120 min. then 150 µL of 1×PBS buffer was injected at a flow rate of 5-30 µL/min to remove the unbound chain in the positive channel. The PDMS layer is torn off and microarray scanner is used to scan the chip. Finally, the lactoferrin-bound ssDNA is eluted by heating with DPEC water at 95° C. for 3-10 min, and the resulting solution was dried to a volume of 25-250 µL with high purity nitrogen at 40-60° C.

(3) PCR amplification process: the solution obtained in step (3) is divided into 3 to 10 parts of the same solution with a volume of 23 µL. Each solution is added with 25 µL of 2×Taq polymerase, 1 µL of 20 µM TAMRA labeled forward primer and 1 µL of 20 µM biotinylated backward primer for PCR amplification.

The product obtained in this step was diluted 5 to 40 times as a template and then amplified again. 5 µL of diluted PCR product with 1 µL of 2×SYBR Premix Ex Taq™ enzyme, 1 µL of 20 µM TAMRA-labeled forward primer, 1 µL of 20 µM biotinylated backward primer and 18 µL of ultrapure water were mixed uniformly for PCR amplification. 10 µL of sample was taken for fluorescence in microplate by BioTek. The round number with highest fluorescence signal was selected to amplify the remaining products.

(4) Separation and purification: The obtained PCR products in step (3) were mixed with 800 µL-5 mL of Promega magnetic beads, the supernatant are removed after rapid shaking for 0.5-2 h. 25 µL of 0.01-0.1 M NaOH solution are added, the double stands are dissociated from the magnetic beads after vortex oscillation for 3-15 min. Then 12.5 µL of 0.1M HCl, 25 µL of DPEC water and 62.5 µL of 2×PBSM buffer solution are added to the supernatant. Neutral solution as a secondary library for the next round of screening with concentration of 40 pmol-100 pmol.

(5) The second round of screening: The library above was sequentially transported into the negative channel at 1-5 µL/min at 25-40° C., and then into the positive channel. Then 150 µL of 1×PBS buffer solution at 5-30 µL/min flow rate to remove unreacted ssDNA sequence in the positive channel. The PDMS layer is gently torn off and Luxscan-10K/A microarray scanner is used to scan the chip. Finally, DPEC water at 95° C. is used to elute the ssDNA sequence bound to the lactoferrin on the chip by heating for 3-10 min, and the obtained solution was dried to 20-250 µL at 60° C. for PCR amplification.

(6) Repeat steps (3), (4), (5) to the eighth round of screening.

(7) The fifth, sixth and seventh rounds of PCR amplification products are sequenced. The above screening process is repeated and the samples are randomly selected for sequencing. All sequences with a repeated sequence greater than 2 are obtained, and the obtained repeated sequences are performed by IDT software. IDT software automatically generates possible secondary structure and ΔG according to the sequence. The end of the sequence will be secondly trimmed to find out a more efficient sequence and a more stable secondary structure (minimum ΔG value) to obtain the optimal aptamer.

In the step (2), the library has 40 random bases in the middle, the nucleotide sequence at the 5' end of the random base is as shown in SEQ ID NO. 1, and the nucleotide sequence at the 3' end of the random base is as shown in SEQ ID NO. 2.

In the step (3), the forward primer has a nucleotide sequence as shown in SEQ ID NO. 3.

The nucleotide sequence of the backward primer is shown in SEQ ID NO. 4.

An aptamer for detecting lactoferrin, wherein the aptamer has a nucleotide sequence as shown in SEQ ID NO. 5-65.

The use of the above aptamers for detecting lactoferrin content in the detection of lactoferrin is within the scope of the present invention.

The principle of the invention: the aptamer is produced by a systematic evolution of ligands by exponential enrichment (SELEX), which can be used to screen specific nucleic acid sequence from random single-stranded nucleic acid sequence libraries. The nucleic acid ligand (aptamer) has highly affinity with the target substance. The invention is based on microarray technology with the large-scale, high-throughput, small volume and microfluidic technology with automatic fluid transport, enhanced molecular reaction efficiency and closed reaction chamber avoiding external pollution. The negative and positive screening process of the aptamer screening are combined on a microfluidic chip, and the aptamer screening can be completed quickly and efficiently. By screening the fluorescence intensity changes after the ssDNA sequence is specifically captured on the positive channel, the evolution of the secondary library with negative screening and positive screening in each screening process can be directly and intuitively monitored. After the method was screened for 7 rounds, aptamer with high affinity are obtained.

The method of screening the aptamers by this microarray microfluidic chip is designed for the first time. Protein microarray production methods, screening libraries and protein array process monitoring are used universally. In addition, PCR process, PCR product purification, secondary library regeneration process are used universally. Therefore, the method of screening aptamers using microarray microfluidic chips has a good general purpose and important research significance.

Beneficial Effects

The invention discloses a method for screening an aptamer by using a microarray microfluidic chip. The screening chip integrates microarray and microfluidic technology to integrate the positive and negative screening process on a microfluidic chip, and obtains aptamer with high affinity after 7 rounds of screening. At the same time, the present invention also discloses specific steps for screening of lactoferrin aptamers, including detailed processes such as chip preparation, positive and negative screening processes, and PCR amplification. The aptamer screened by the method has good specificity and affinity to the target protein. The aptamer is easier to be obtained than the antibody, and can be synthesized rapidly in large quantities in vitro. The preparation method is simpler and faster, so aptamers are expected to be a useful complement to antibody technology in many areas. In addition, the chip mode consisting of positive and negative screening is convenient, fast and efficient. It can also be used for screening aptamers towards other proteins, and provides a good idea design and reference for other aptamer screening workers.

DETAILED DESCRIPTION OF INVENTION

Figure 1:
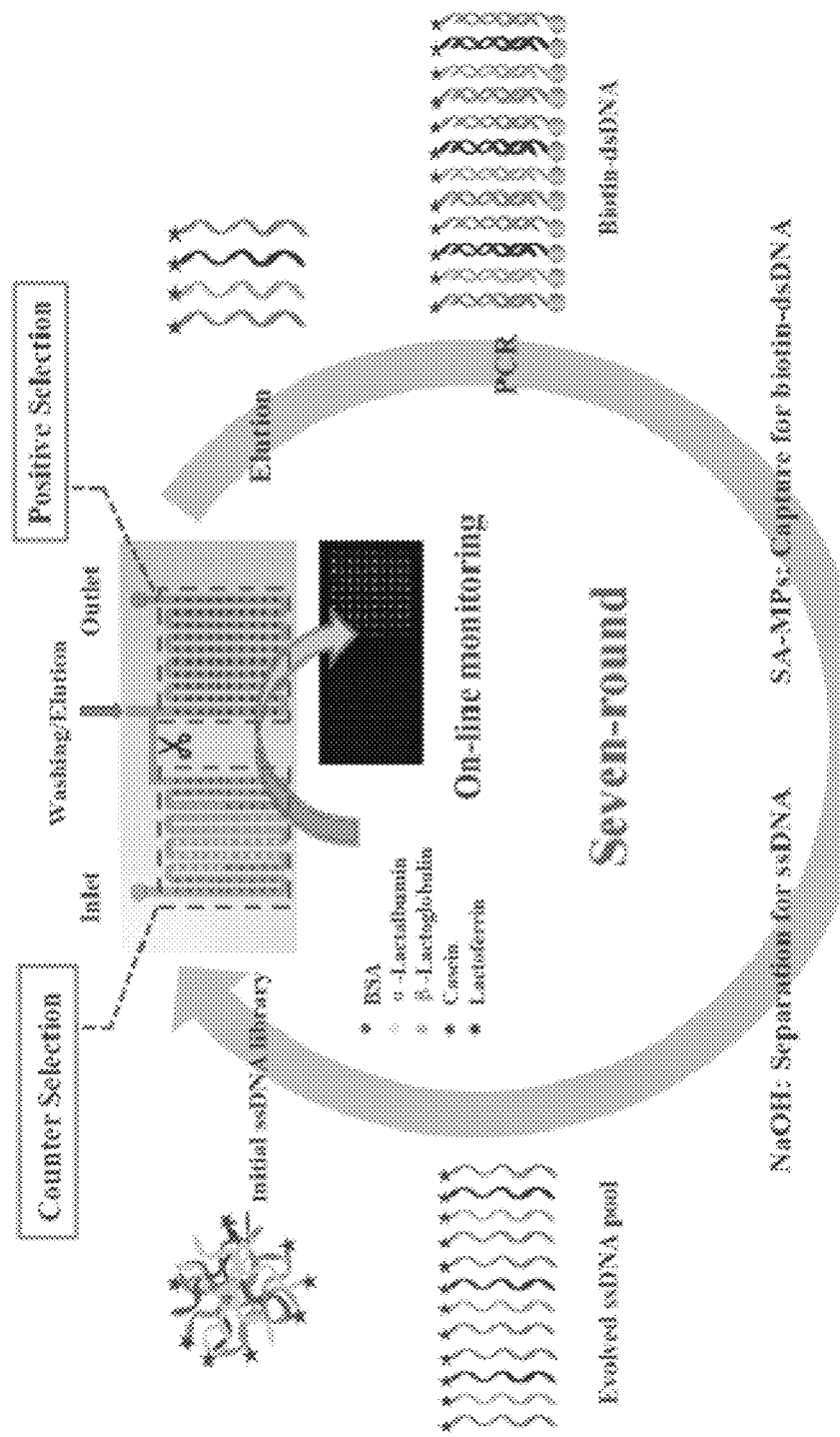
FIG. 1 Schematics of aptamer screening based on microarray microfluidics.
Figure 2:
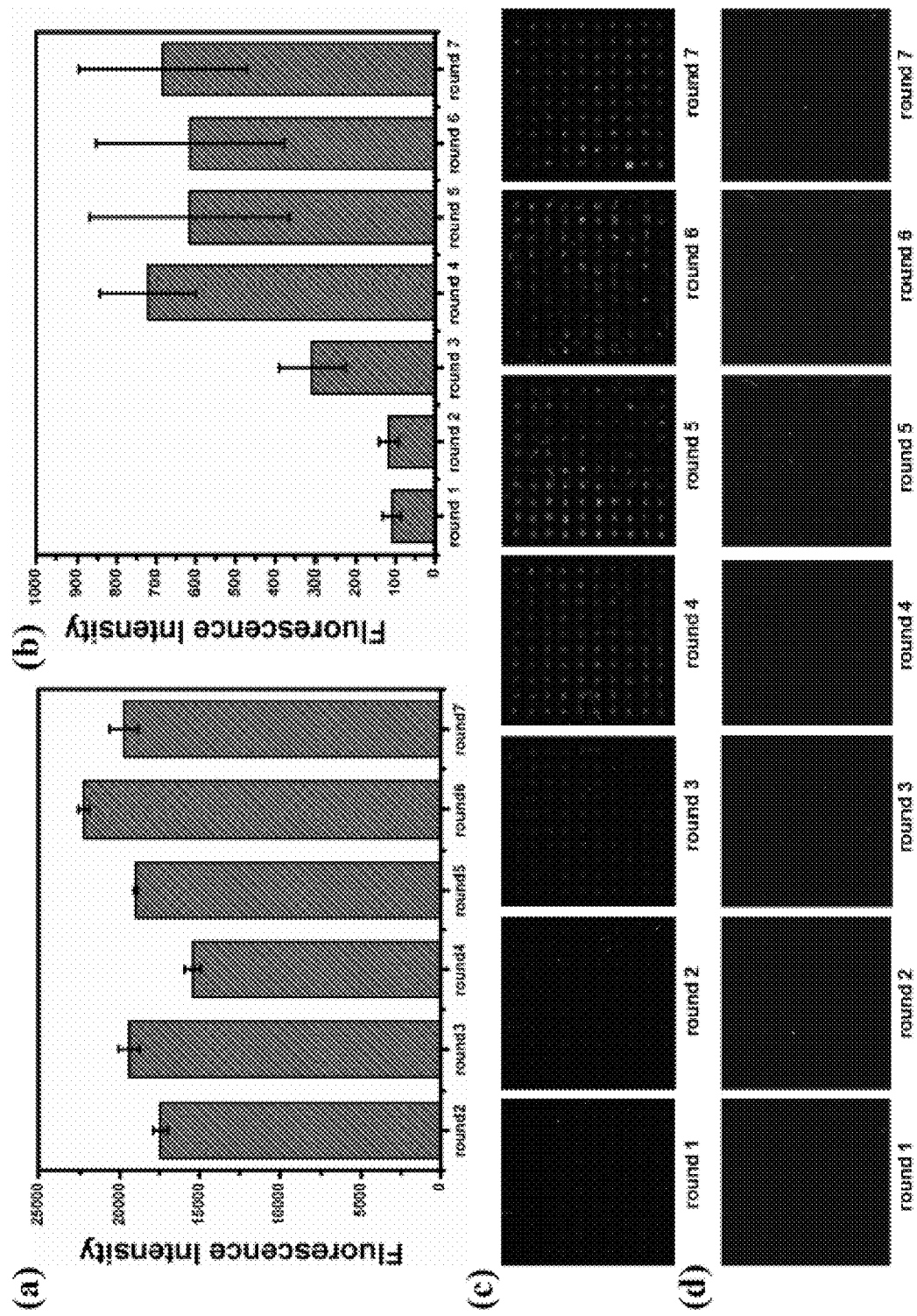
FIG. 2. Results of the first screening, (a) amount of library per round, (b) fluorescence signal intensity of the aptamer on the chip, (c) imaging image of the aptamer on the chip, (d) Image after chip cleaning.
Figure 3:
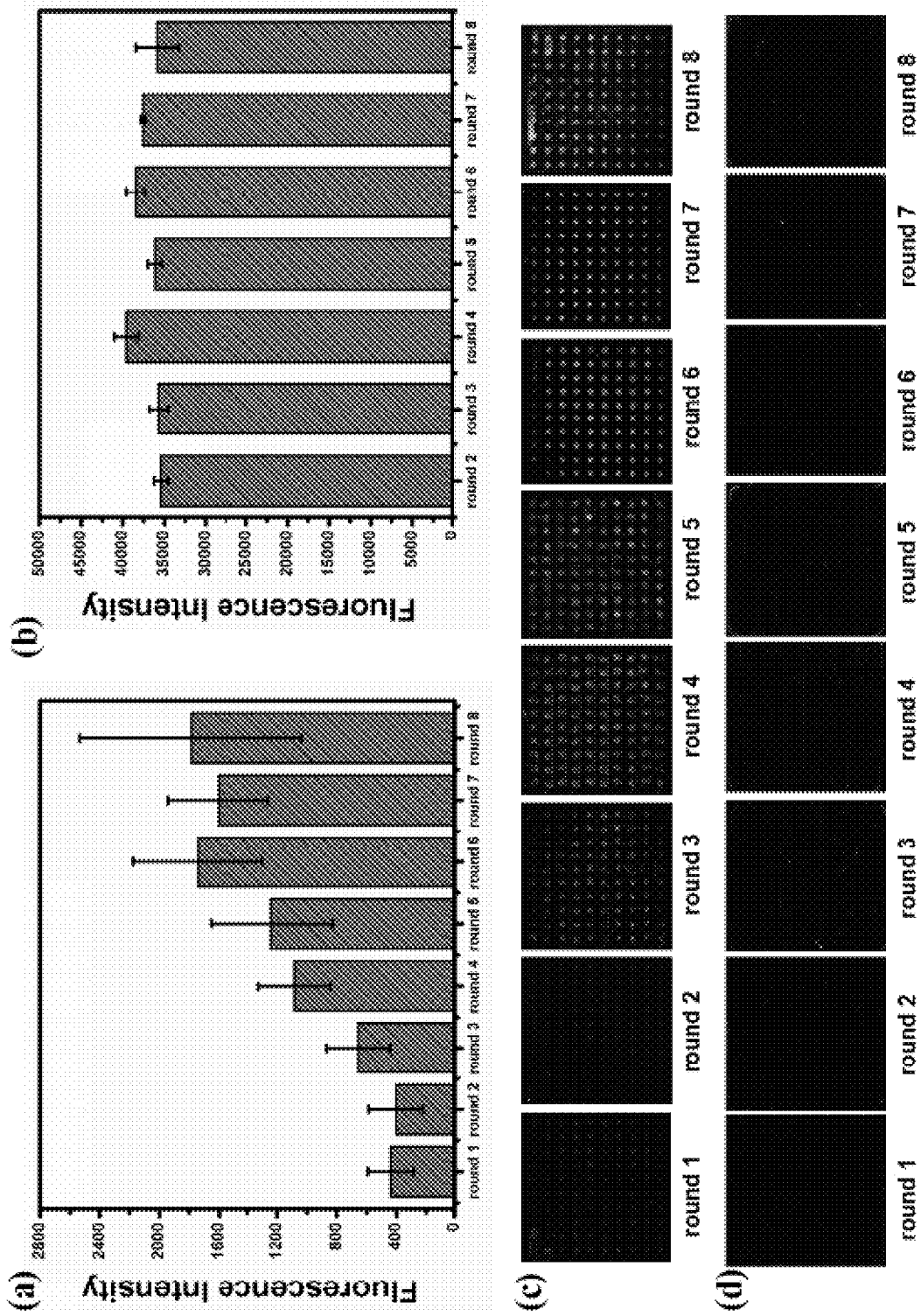
FIG. 3. Results of the second screening, (a) amount of library per round, (b) fluorescence signal intensity of the aptamer on the chip, (c) imaging image of the aptamer on the chip, (d) Image image after chip cleaning.
Figure 4:
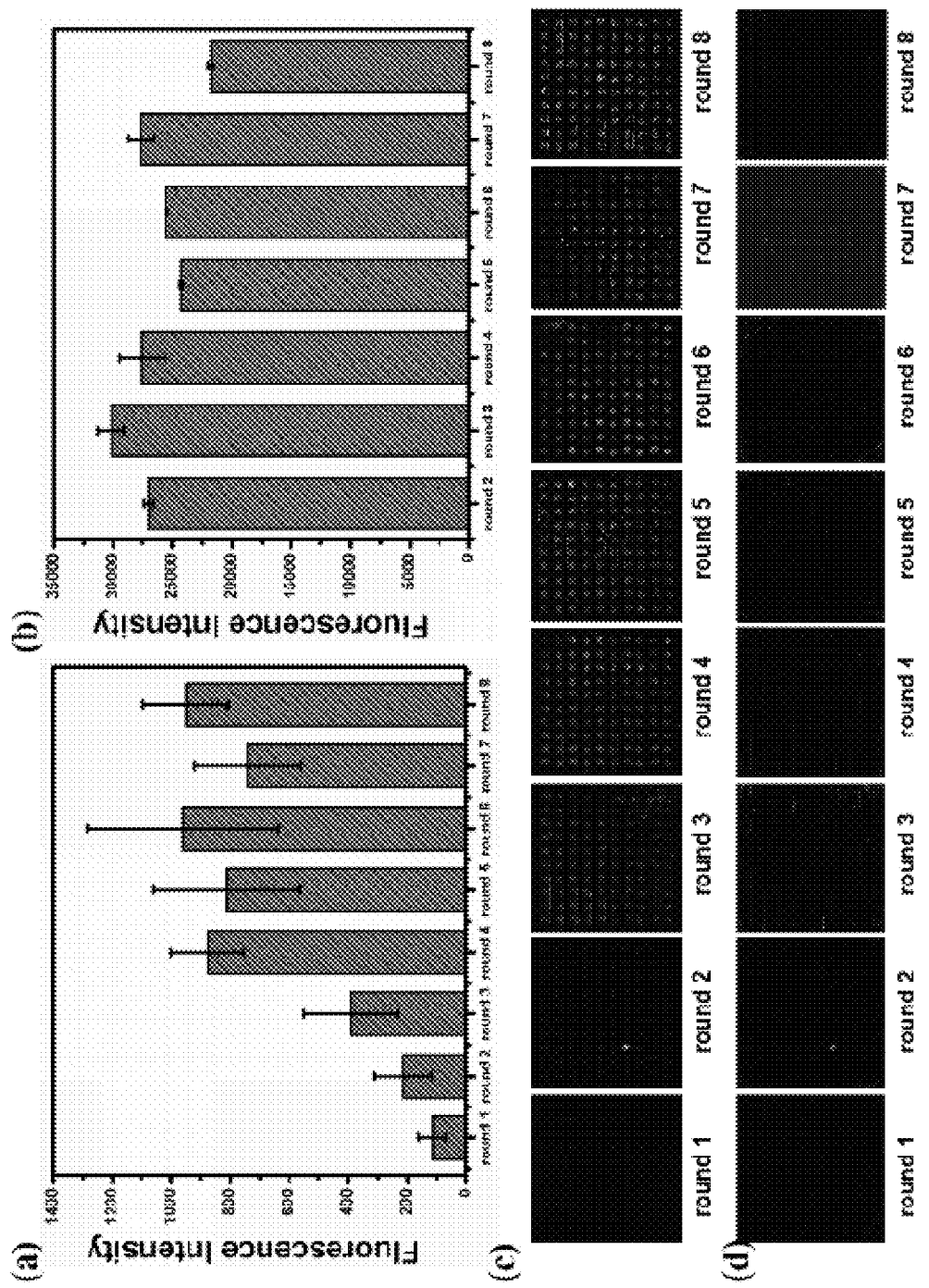
FIG. 4. Results of the third screening, (a) amount of library per round, (b) fluorescence signal intensity of the aptamer on the chip, (c) imaging image of the aptamer on the chip, (d)) Image image after chip cleaning.

The invention can be better understood in light of the following examples. However, those skilled in the art will understand that the description of the embodiments is only intended to illustrate the invention and should not be construed as limiting the invention as described in the claims.

Example 1: Preparation of Microarray Microfluidic Chip

Chip preparation: The microfluidic channel template was fabricated by the combination of lithography mask and chemical etching, and was reserved for the subsequent PDMS channel preparation. The PDMS pre-polymer and the curing agent are mixed at a mass ratio of 10:1. After vacuuming, it was poured onto a microfluidic channel template to obtain a PDMS microfluidic channel. A spotting instrument was used to prepare a 5 mg/mL of lactoferrin and a negative protein microarray on a glass substrate. PDMS and the spotted glass substrate are simultaneously plasma treated, and then closely adhered together as a screening chip for the next round of screening.

Example 2: PCR Amplification

The eluted solution on the chip was divided into 6 equal volumes of 23 µL, each of which was sequentially added with 25 µL of 2×Taq polymerase, 1 µL of 20 µM TAMRA-labeled forward primer and 1 µL of 20 µM biotinylated backward primers for PCR amplification. PCR thermal cycling is as follows: 94° C. for 5 min, cycling 94° C. for 30 s, 60.5° C. for 30 s, 72° C. for 30 s with 10 rounds. The reaction was stopped at 72° C. for 5 min. The product obtained in this step was diluted 10-fold and then amplified as a template. 5 µL of the diluted PCR product, 1 µL of 2×SYBR Premix Ex Taq™ enzyme, 1 µL of 20 µM TAMRA labeled before Primer, 1 µL of 20 µM biotinylated backward primer and 18 µL of ultrapure water were mixed well. 10 µL of sample in every round was taken for fluorescence in microplate by BioTek. The round number with highest fluorescence signal was selected to amplify the remaining products.

Example 3: Screening of Lactoferrin Aptamers

The specific steps of screening the lactoferrin aptamer include detailed processes such as chip preparation, positive and negative screening process, and PCR amplification, as described below, wherein:

```
Library:
                                       (SEQ ID NO: 66)
5'-TAMRA-GACAGGCAGGACACCGTAAC-N40-
CTGCTACCTCCCTCCTCTTC-3'

TARMA modified forward primer:
                                       (SEQ ID NO: 3)
5'-TARMA-GACAGGCAGGACACCGTAAC-3'

Biotinylated backward primer:
                                       (SEQ ID NO: 4)
5'Biotin-GAAGAGGAGGGAGGTAGCAG-3'
```

(1) Chip preparation: The microfluidic channel template was fabricated by the combination of lithography mask and chemical etching, and was reserved for the subsequent PDMS channel preparation.

The PDMS prepolymer and the curing agent are mixed at a mass ratio of 10:1. After vacuuming, it was poured onto a microfluidic channel template to obtain a PDMS microfluidic channel. A spotting instrument was used to prepare a 5 mg/mL of lactoferrin and a negative protein microarray on a glass substrate. PDMS and the spotted glass substrate are simultaneously plasma treated, and then closely adhered together as a screening chip for the next round of screening.

(2) Screening preparation: The screening chip obtained in step (1) was placed in a constant temperature water bath for incubation for 2 h at 37° C. Then 20 mg/ml of BSA and 0.01 mM of random sequence short-chain ssDNA (20 nt) were introduced and incubated at 37° C. for 1 h. Then, 150 µL of 1×PBST solution was used to clean the positive and negative screen channels.

(3) First round of screening: 0.5 nmol, 125 µL of the original library was heated at 95° C. for 5 min, and immediately frozen on ice for 10 s. Then the syringe was used to deliver the library into the positive channel at a flow rate of 2.5 µL/min. The reaction was carried out at room temperature for 50 min. Then 150 µL of 1×PBS buffer solution was passed at a flow rate of 15 µL/min to remove the unbound ssDNA sequence in the positive channel. The PDMS layer was gently torn off and Luxscan-10K/A microarray scanner is used to scan the chip. Finally, the lactoferrin-bound ssDNA sequence is eluted with DPEC water at 95° C. for 5 min, and the resulting solution is dried to a volume of 69 µL under high purity nitrogen at 50° C.

(4) PCR amplification process: the solution obtained in step (3) is divided into 3 parts of the same solution with a volume of 23 µL. Each step is added with 25 µL of 2×Taq polymerase, 1 µL of 20 µM TAMRA labeled forward primers and 1 µL of 20 µM biotinylated backward primers and the mixture were PCR-amplified. PCR thermal cycling is as follows: 94° C. for 5 min, cycling 94° C. for 30 s, 60.5° C. for 30 s, 72° C. 30 s for 10 rounds and terminated at 72° C. for 5 min. The product obtained in this step is diluted 10 times and then amplified as a template: 5 µL of the diluted PCR product and 1 µL of 2×SYBR Premix Ex Taq™ enzyme, 1 µL of 20 µM TAMRA-labeled forward primer, 1 µL of 20 µM biotinylated backward primer and 18 µL DPEC water were mixed well. 10 µL of sample in every round was taken for fluorescence in microplate by BioTek. The round number with highest fluorescence signal was selected to amplify the remaining products.

(5) Separation and purification: Mix the PCR product obtained in step (4) with 600 µL of Promega beads, shake the plate for 1 h and remove the supernatant. Then 25 µL of 50 mM NaOH is added to vortex for 5 min. The double strands attached to the magnetic beads were dissociated, the supernatant was aspirated and sequentially added with 12.5 µL of 100 mM HCl, 25 µL of $H_2O$, 62.5 µL of 2×PBSM, and the resulting solution was used as a secondary library for the next round of screening. The content is about 40 pmol.

(6) The second round of screening: The library was pumped into the negative channel at a flow rate of 2.5 µL/min, and reacted at room temperature for 50 min. Then the pump was used to input the library into the positive channel at a flow rate of 2.5 µL/min. The reaction was carried out at room temperature for 50 min. Then 150 µL of 1×PBS buffer solution is passed at a flow rate of 15 µL/min to remove unreacted chains in the positive channel. The PDMS layer is gently torn off and Luxscan-10K/A microarray scanner is used to scan the chip. Finally, the protein-bound chain was eluted by heating with non-nuclear water at 95° C. for 5 min, and the resulting solution was dried at 60° C. to a volume of 92 µL, which was left for PCR amplification;

(7) Repeat steps (4), (5), (6) to the eighth round of screening;

(8) The fifth, sixth and seventh rounds of PCR amplification products are sent to Shanghai Biotech for sequencing. 120 rounds of sequencing are randomly selected in each round, and the obtained chains are analyzed by IDT software for secondary structure analysis. The optimal aptamers are obtained.

Example 4: Screening of Lactoferrin Aptamers

The specific steps of screening the lactoferrin aptamer include detailed processes such as chip preparation, positive and negative screening process, and micro PCR amplification, as described below, wherein:

```
Library:
                                       (SEQ ID NO: 66)
5'-TAMRA-GACAGGCAGGACACCGTAAC-N40-
CTGCTACCTCCCTCCTCTTC-3'

TARMA modified forward primer:
                                       (SEQ ID NO: 3)
5'-TARMA-GACAGGCAGGACACCGTAAC-3'

Biotinylated backward primer:
                                       (SEQ ID NO: 4)
5'Biotin-GAAGAGGAGGGAGGTAGCAG-3'
```

(1) Chip preparation: The microfluidic channel template was fabricated by the combination of lithography mask and chemical etching, and was reserved for the subsequent PDMS channel preparation. The PDMS prepolymer and the curing agent are mixed at a mass ratio of 10:1. After vacuuming, it was poured onto a microfluidic channel template to obtain a PDMS microfluidic channel. A spotting instrument was used to prepare a 2.5 mg/mL of lactoferrin and a negative protein microarray on a glass substrate. PDMS and the spotted glass substrate are simultaneously plasma treated, and then closely adhered together as a screening chip for the next round of screening.

(2) Screening preparation: The screening chip obtained in step (1) was placed in a constant temperature water bath for incubation for 3 h at 37° C. Then 20 mg/ml of BSA and 0.01 mM of random sequence short-chain ssDNA (20 nt) were introduced and incubated at 37° C. for 2 h. Then, 150 µL of 1×PBST solution was used to clean the positive and negative screen channels.

(3) First round of screening: 1 nmol, 125 µL of the original library was heated at 95° C. for 5 min, and immediately frozen on ice for 10 s. Then the syringe was used to deliver the library into the positive channel at a flow rate of 2.5 µL/min. The reaction was carried out at room temperature for 50 min. Then 150 µL of 1×PBS buffer solution was passed at a flow rate of 15 µL/min to remove the unbound ssDNA sequence in the positive channel. The PDMS layer was gently torn off and Luxscan-10K/A microarray scanner is used to scan the chip. Finally, the lactoferrin-bound ssDNA sequence is eluted with DPEC water at 95° C. for 5 min, and the resulting solution is dried to a volume of 92 µL under high purity nitrogen at 50° C.

(4) PCR amplification process: the solution obtained in step (3) is divided into 4 parts of the same solution with a volume of 23 µL. Each step is added with 25 µL of 2×Taq polymerase, 1 µL of 20 µM TAMRA labeled forward primers and 1 µL of 20 µM biotinylated backward primers and the mixture were PCR-amplified. PCR thermal cycling is as follows: 94° C. for 5 min, cycling 94° C. for 30 s, 60.5° C. for 30 s, 72° C. 30 s for 10 rounds and terminated at 72° C. for 5 min. The product obtained in this step is diluted 10 times and then amplified as a template: 5 µL of the diluted PCR product and 1 µL of 2×SYBR Premix Ex Taq™ enzyme, 1 µL of 20 µM TAMRA-labeled forward primer, 1 µL of 20 µM biotinylated backward primer and 18 µL DPEC water were mixed well. 10 µL of sample in every round was taken for fluorescence in microplate by BioTek. The round number with highest fluorescence signal was selected to amplify the remaining products.

(5) Separation and purification: Mix the PCR product obtained in step (4) with 800 µL of Promega beads, shake the plate for 1 h and remove the supernatant. Then 25 µL of 1 M NaOH is added to vortex for 5 min. The double strands attached to the magnetic beads were dissociated, the supernatant was aspirated and sequentially added with 12.5 µL of 2 M HCl, 25 µL of $H_2O$, 62.5 µL of 2×PBSM, and the resulting solution was used as a secondary library for the next round of screening. The content is about 90 pmol.

(6) The second round of screening: The library was pumped into the negative channel at a flow rate of 2.5 µL/min, and reacted at room temperature for 50 min. Then the pump was used to input the library into the positive channel at a flow rate of 2.5 µL/min. The reaction was carried out at room temperature for 50 min. Then 150 µL of 1×PBS buffer solution is passed at a flow rate of 15 µL/min to remove unreacted chains in the positive channel. The PDMS layer is gently torn off and Luxscan-10K/A microarray scanner is used to scan the chip. Finally, the protein-bound chain was eluted by heating with non-nuclear water at 95° C. for 5 min, and the resulting solution was dried at 60° C. to a volume of 92 µL, which was left for PCR amplification;

(7) Repeat steps (4), (5), (6) to the eighth round of screening;

(8) The fifth, sixth and seventh rounds of PCR amplification products are sent to Shanghai Biotech for sequencing. 120 rounds of sequencing are randomly selected in each round, and the obtained chains are analyzed by IDT software for secondary structure analysis. The optimal aptamers are obtained.

Example 5: Screening of Lactoferrin Aptamers

The specific steps of screening the lactoferrin aptamer include detailed processes such as chip preparation, positive and negative screening process, and micro PCR amplification, as described below, wherein:

```
Library:
                                    (SEQ ID NO: 66)
5'-TAMRA-GACAGGCAGGACACCGTAAC-N40-
CTGCTACCTCCCTCCTCTTC-3'

TARMA modified forward primer:
                                    (SEQ ID NO: 3)
5'-TARMA-GACAGGCAGGACACCGTAAC-3'

Biotinylated backward primer:
                                    (SEQ ID NO: 4)
5'Biotin-GAAGAGGAGGGAGGTAGCAG-3'
```

(1) Chip preparation: The microfluidic channel template was fabricated by the combination of lithography mask and chemical etching, and was reserved for the subsequent PDMS channel preparation. The PDMS pre-polymer and the curing agent are mixed at a mass ratio of 10:1. After vacuuming, it was poured onto a microfluidic channel template to obtain a PDMS microfluidic channel. A spotting instrument was used to prepare a 5 mg/mL of lactoferrin and a negative protein microarray on a glass substrate. PDMS and the spotted glass substrate are simultaneously plasma treated, and then closely adhered together as a screening chip for the next round of screening.

(2) Screening preparation: The screening chip obtained in step (1) was placed in a constant temperature water bath for incubation for 2 h at 37° C. Then 20 mg/ml of BSA and 0.01 mM of random sequence short-chain ssDNA (20 nt) were introduced and incubated at 37° C. for 1 h. Then, 150 µL of 1×PBST solution was used to clean the positive and negative screen channels.

(3) First round of screening: 1 nmol, 125 µL of the original library was heated at 95° C. for 5 min, and immediately frozen on ice for 10 s. Then the syringe was used to deliver the library into the positive channel at a flow rate of 5 µL/min. The reaction was carried out at room temperature for 50 min. Then 150 µL of 1×PBS buffer solution was passed at a flow rate of 30 µL/min to remove the unbound ssDNA sequence in the positive channel. The PDMS layer was gently torn off and Luxscan~10K/A microarray scanner is used to scan the chip. Finally, the lactoferrin-bound ssDNA sequence is eluted with DPEC water at 95° C. for 5 min, and the resulting solution is dried to a volume of 92 µL under high purity nitrogen at 50° C.

(4) PCR amplification process: the solution obtained in step (3) is divided into 4 parts of the same solution with a volume of 23 µL. Each step is added with 25 µL of 2×Taq polymerase, 1 µL of 20 µM TAMRA labeled forward primers and 1 µL of 20 µM biotinylated backward primers and the mixture were PCR-amplified. PCR thermal cycling is as follows: 94° C. for 5 min, cycling 94° C. for 30 s, 60.5° C. for 30 s, 72° C. 30 s for 10 rounds and terminated at 72° C. for 5 min. The product obtained in this step is diluted 10 times and then amplified as a template: 5 µL of the diluted PCR product and 1 µL of 2×SYBR Premix Ex Taq™ enzyme, 1 µL of 20 µM TAMRA-labeled forward primer, 1 µL of 20 µM biotinylated backward primer and 18 µL DPEC water were mixed well. 10 µL of sample in every round was taken for fluorescence in microplate by BioTek. The round number with highest fluorescence signal was selected to amplify the remaining products.

(5) Separation and purification: Mix the PCR product obtained in step (4) with 800 µL of Promega beads, shake the plate for 1 h and remove the supernatant. Then 25 µL of 50 mM NaOH is added to vortex for 5 min. The double strands attached to the magnetic beads were dissociated, the supernatant was aspirated and sequentially added with 12.5 µL of 100 mM HCl, 25 µL of $H_2O$, 62.5 µL of 2×PBSM, and the resulting solution was used as a secondary library for the next round of screening. The content is about 60 pmol.

(6) The second round of screening: The library was pumped into the negative channel at a flow rate of 5 µL/min, and reacted at room temperature for 50 min. Then the pump was used to input the library into the positive channel at a flow rate of 5 µL/min. The reaction was carried out at room temperature for 50 min. Then 150 µL of 1×PBS buffer solution is passed at a flow rate of 30 µL/min to remove unreacted chains in the positive channel. The PDMS layer is gently torn off and Luxscan-10K/A microarray scanner is used to scan the chip. Finally, the protein-bound chain was eluted by heating with non-nuclear water at 95° C. for 5 min, and the resulting solution was dried at 60° C. to a volume of 92 µL, which was left for PCR amplification;

(7) Repeat steps (4), (5), (6) to the eighth round of screening;

(8) The fifth, sixth and seventh rounds of PCR amplification products are sent to Shanghai Biotech for sequencing. 120 rounds of sequencing are randomly selected in each round, and the obtained chains are analyzed by IDT software for secondary structure analysis. The optimal aptamers are obtained.

Example 6: Screening of Lactoferrin Aptamers

The specific steps of screening the lactoferrin aptamer include detailed processes such as chip preparation, positive and negative screening process, and micro PCR amplification, as described below, wherein:

```
Library:
                                    (SEQ ID NO: 66)
5'-TAMRA-GACAGGCAGGACACCGTAAC-N40-
CTGCTACCTCCCTCCTCTTC-3'

TARMA modified forward primer:
                                    (SEQ ID NO: 3)
5'-TARMA-GACAGGCAGGACACCGTAAC-3'

Biotinylated backward primer:
                                    (SEQ ID NO: 4)
5'Biotin-GAAGAGGAGGGAGGTAGCAG-3'
```

(1) Chip preparation: The microfluidic channel template was fabricated by the combination of lithography mask and chemical etching, and was reserved for the subsequent PDMS channel preparation. The PDMS prepolymer and the curing agent are mixed at a mass ratio of 10:1. After vacuuming, it was poured onto a microfluidic channel template to obtain a PDMS microfluidic channel. A spotting instrument was used to prepare a 5 mg/mL of lactoferrin and a negative protein microarray on a glass substrate. PDMS and the spotted glass substrate are simultaneously plasma treated, and then closely adhered together as a screening chip for the next round of screening.

(2) Screening preparation: The screening chip obtained in step (1) was placed in a constant temperature water bath for incubation for 2 h at 37° C. Then 20 mg/ml of BSA and 0.01 mM of random sequence short-chain ssDNA (20 nt) were introduced and incubated at 37° C. for 1 h. Then, 150 µL of 1×PBST solution was used to clean the positive and negative screen channels.

(3) First round of screening: 1 nmol, 125 µL of the original library was heated at 95° C. for 5 min, and immediately frozen on ice for 10 s. Then the syringe was used to deliver the library into the positive channel at a flow rate of 2.5 µL/min. The reaction was carried out at room temperature for 50 min. Then 150 µL of 1×PBS buffer solution was passed at a flow rate of 15 µL/min to remove the unbound ssDNA sequence in the positive channel. The PDMS layer was gently torn off and Luxscan-10K/A microarray scanner is used to scan the chip. Finally, the lactoferrin-bound ssDNA sequence is eluted with DPEC water at 95° C. for 5 min, and the resulting solution is dried to a volume of 92 µL under high purity nitrogen at 50° C.

(4) PCR amplification process: the solution obtained in step (3) is divided into 4 parts of the same solution with a volume of 23 µL. Each step is added with 25 µL of 2×Taq polymerase, 1 µL of 20 µM TAM RA labeled forward primers and 1 µL of 20 µM biotinylated backward primers and the mixture were PCR-amplified. PCR thermal cycling is as follows: 94° C. for 5 min, cycling 94° C. for 30 s, 60.5° C. for 30 s, 72° C. 30 s for 10 rounds and terminated at 72° C. for 5 min. The product obtained in this step is diluted 10 times and then amplified as a template: 5 µL of the diluted PCR product and 1 µL of 2×SYBR Premix Ex Taq™ enzyme, 1 µL of 20 µM TAMRA-labeled forward primer, 1 µL of 20 µM biotinylated backward primer and 18 µL DPEC water were mixed well. 10 µL of sample in every round was taken for fluorescence in microplate by BioTek. The round number with highest fluorescence signal was selected to amplify the remaining products.

(5) Separation and purification: Mix the PCR product obtained in step (4) with 800 µL of Promega beads, shake the plate for 1 h and remove the supernatant. Then 25 µL of 50 mM NaOH is added to vortex for 5 min. The double strands attached to the magnetic beads were dissociated, the supernatant was aspirated and sequentially added with 12.5 µL of 100 mM HCl, 25 µL of $H_2O$, 62.5 µL of 2×PBSM, and the resulting solution was used as a secondary library for the next round of screening. The content is about 60 pmol.

(6) The second round of screening: The library was pumped into the negative channel at a flow rate of 5 µL/min, and reacted at room temperature for 50 min. Then the pump was used to input the library into the positive channel at a flow rate of 5 µL/min. The reaction was carried out at room temperature for 50 min. Then 150 µL of 1×PBS buffer solution is passed at a flow rate of 30 µL/min to remove unreacted chains in the positive channel. The PDMS layer is gently torn off and Luxscan-10K/A microarray scanner is used to scan the chip. Finally, the protein-bound chain was eluted by heating with non-nuclear water at 95° C. for 5 min, and the resulting solution was dried at 60° C. to a volume of 92 µL, which was left for PCR amplification;

(7) Repeat steps (4), (5), (6) to the eighth round of screening;

(8) The fifth, sixth and seventh rounds of PCR amplification products are sent to Shanghai Biotech for sequencing. 120 rounds of sequencing are randomly selected in each round, and the obtained chains are analyzed by IDT software for secondary structure analysis. The optimal aptamers are obtained. The sequence of the resulting test aptamer is shown in SEQ ID NO. 5 to SEQ ID NO. 65.

Example 7: Detection of Lactoferrin Standard Samples by Fluorescence Polarization (1) 100 μL of 25 μg/mL lactoferrin standard sample is mixed with 10 μL of 250 nM FITC (fluorescein isothiocyanate)-labeled aptamer N2 (base sequence: AGGCAGGACACCGTAACCGGTGCATCTATGGC-TACTAGCTTTTCCTGCCT) (SEQ ID NO: 06).

(2) The mixture of step (1) is placed in a 96-well plate at 37° C. for 15 min, and directly scanned with a BioTeK microplate reader. The excitation wavelength is 480 nm and the emission wavelength is 528 nm.

Example 8: Method for Detecting Lactoferrin Content (1) 25-100 fold diluted milk sample is mixed with 10 μL of 250 nM FITC solution (fluorescein isothiocyanate)-labeled aptamer N2 (base sequence: AGGCAGGACACCGTAACCGGTGCATCTATGGC-TACTAGCTTTTCCTGCCT) (SEQ ID NO: 06).

(2) The mixture of the step (1) is placed in a 96-well plate at 37° C. for 15 min, and directly scanned with a BioTeK microplate reader with an excitation wavelength of 480 nm and an emission wavelength of 528 nm.

(3) Compare the standard curve to obtain the concentration of lactoferrin in the milk sample.

Example 9: Method for Detecting Lactoferrin Content (1) 25-100 fold diluted milk sample is mixed with 10 μL of 250 nM FITC solution (fluorescein isothiocyanate)-labeled aptamer N6 (base sequence: gcaggacacc gtaactcggg caaagctctg aataatgttc aaccaatatt ctgtcctgc) (SEQ ID NO: 10), and mix well.

(2) The mixture of the step (1) is placed in a 96-well plate at 37° C. for 15 min, and directly scanned with a BioTeK microplate reader with an excitation wavelength of 480 nm and an emission wavelength of 528 nm.

Figure 5:
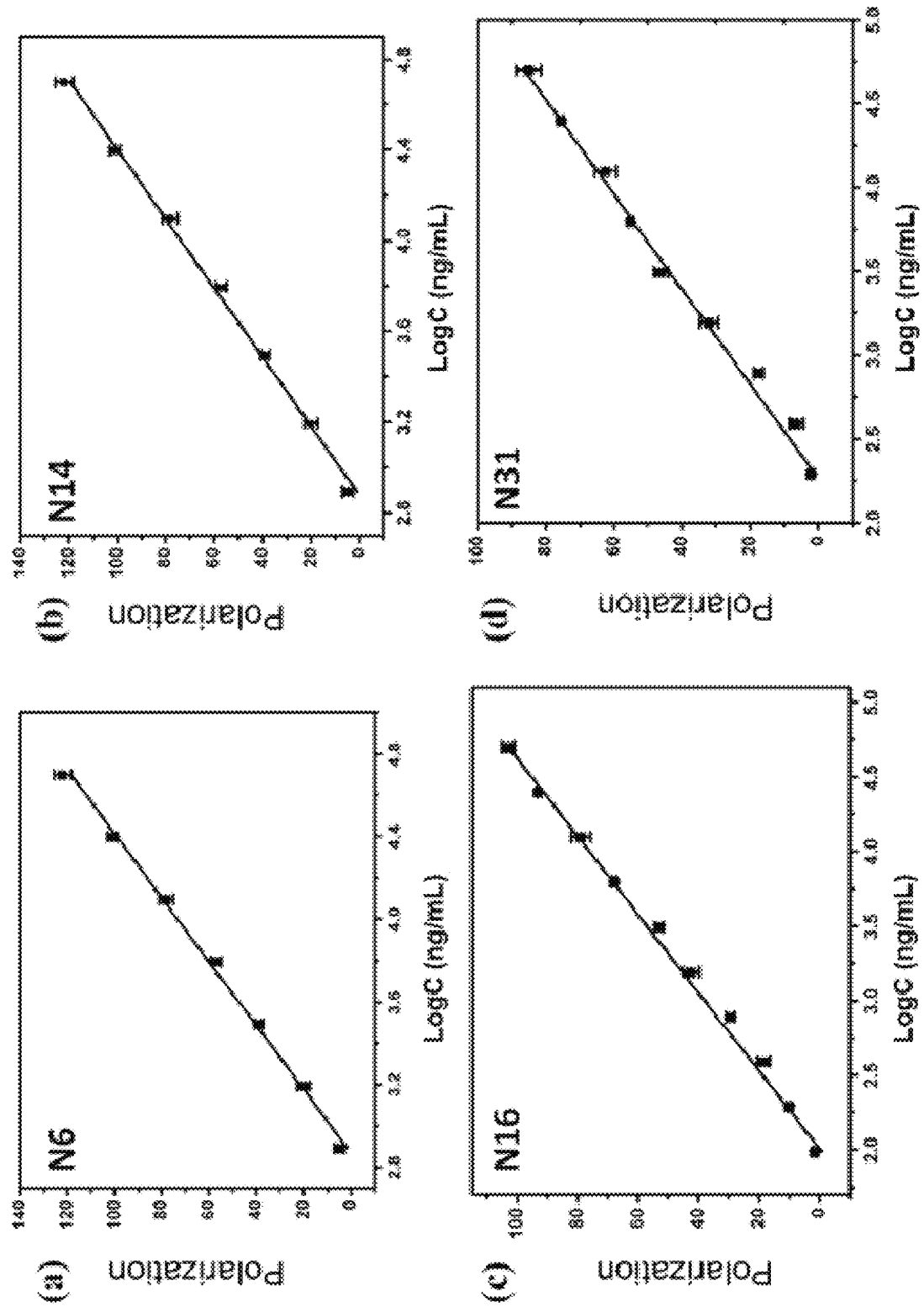
FIG. 5. A linear plot of other aptamers for lactoferrin detection by fluorescence polarization: (a) a polarization plot for aptamer N2, (b) a polarization plot for aptamer N14, (c) a polarization plot for aptamer N16 and (d) a polarization plot for aptamer N31.

(3) Compare the standard curve to obtain the concentration of lactoferrin in the milk sample, as shown in FIG. 5(a).

Example 10: Method for Detecting Lactoferrin Content (1) 25-100 fold diluted milk sample is mixed with 10 μL of 250 nM FITC solution (fluorescein isothiocyanate)-labeled aptamer N14 (base sequence: gcaggacacc gtaacactgc ttatccccg tcggcttggc tcttcgacag tgtggctgc) (SEQ ID NO: 18), and mix well.

(2) The mixture of the step (1) is placed in a 96-well plate at 37° C. for 15 min, and directly scanned with a BioTeK microplate reader with an excitation wavelength of 480 nm and an emission wavelength of 528 nm.

(3) Compare the standard curve to obtain the concentration of lactoferrin in the milk sample, as shown in FIG. 5(b).

Example 11: Method for Detecting Lactoferrin Content (1) 25-100 fold diluted milk sample is mixed with 10 μL of 250 nM FITC solution (fluorescein isothiocyanate)-labeled aptamer N16 (base sequence: ggcaggacac cgtaaccct agttcctggt gcatttatgg caaagctttt cctgcc) (SEQ ID NO: 20), and mix well.

(2) The mixture of the step (1) is placed in a 96-well plate at 37° C. for 15 min, and directly scanned with a BioTeK microplate reader with an excitation wavelength of 480 nm and an emission wavelength of 528 nm.

(3) Compare the standard curve to obtain the concentration of lactoferrin in the milk sample, as shown in FIG. 5(c).

Example 12: Method for Detecting Lactoferrin Content (1) 25-100 fold diluted milk sample is mixed with 10 μL of 250 nM FITC solution (fluorescein isothiocyanate)-labeled aptamer N31 (ggcaggacac cgtaaccagt ataggtgcat ttttggcgca agctcttcct gccctg) (SEQ ID NO: 35), and mix well.

(2) The mixture of the step (1) is placed in a 96-well plate at 37° C. for 15 min, and directly scanned with a BioTeK microplate reader with an excitation wavelength of 480 nm and an emission wavelength of 528 nm.

(3) Compare the standard curve to obtain the concentration of lactoferrin in the milk sample, as shown in FIG. 5(d).

Example 13: Screening of α-Lactalbumin Aptamers

The specific steps of the α-lactalbumin aptamer screening include detailed processes such as chip preparation, positive and negative screening process, and PCR amplification, as described below, wherein:

```
Library:
                                   (SEQ ID NO: 66)
5'-TAMRA-GACAGGCAGGACACCGTAAC-N40-
CTGCTACCTCCCTCCTCTTC-3'

TARMA modified forward primer:
                                   (SEQ ID NO: 3)
5'-TARMA-GACAGGCAGGACACCGTAAC-3'

Biotinylated backward primer:
                                   (SEQ ID NO: 4)
5'Biotin-GAAGAGGAGGGAGGTAGCAG-3'
```

(1) Chip preparation: The microfluidic channel template was fabricated by the combination of lithography mask and chemical etching, and was reserved for the subsequent PDMS channel preparation. The PDMS prepolymer and the curing agent are mixed at a mass ratio of 10:1. After vacuuming, it was poured onto a microfluidic channel template to obtain a PDMS microfluidic channel. A spotting instrument was used to prepare a 5 mg/mL of lactoferrin and a negative protein microarray on a glass substrate. PDMS and the spotted glass substrate are simultaneously plasma treated, and then closely adhered together as a screening chip for the next round of screening.

(2) Screening preparation: The screening chip obtained in step (1) was placed in a constant temperature water bath for incubation for 2 h at 37° C. Then 20 mg/ml of BSA and 0.01 mM of random sequence short-chain ssDNA (20 nt) were introduced and incubated at 37° C. for 1 h. Then, 150 μL of 1×PBST solution was used to clean the positive and negative screen channels.

(3) First round of screening: 0.5 nmol, 125 μL of the original library was heated at 95° C. for 5 min, and immediately frozen on ice for 10 s. Then the syringe was used to deliver the library into the positive channel at a flow rate of 2.5 μL/min. The reaction was carried out at room temperature for 50 min. Then 150 μL of 1×PBS buffer solution was passed at a flow rate of 15 μL/min to remove the unbound ssDNA sequence in the positive channel. The PDMS layer was gently torn off and Luxscan-10K/A microarray scanner is used to scan the chip. Finally, the α-lactalbumin-bound ssDNA sequence is eluted with DPEC water at 95° C. for 5 min, and the resulting solution is dried to a volume of 92 μL under high purity nitrogen at 50° C.

(4) PCR amplification process: the solution obtained in step (3) is divided into 4 parts of the same solution with a volume of 23 μL. Each step is added with 25 μL of 2×Taq polymerase, 1 μL of 20 μM TAMRA labeled forward primers and 1 μL of 20 μM biotinylated backward primers and the mixture were PCR-amplified. PCR thermal cycling is as follows: 94° C. for 5 min, cycling 94° C. for 30 s, 60.5° C. for 30 s, 72° C. 30 s for 10 rounds and terminated at 72° C. for 5 min. The product obtained in this step is diluted 10 times and then amplified as a template: 5 μL of the diluted PCR product and 1 μL of 2×SYBR Premix Ex Taq™ enzyme, 1 μL of 20 μM TAMRA-labeled forward primer, 1 μL of 20 μM biotinylated backward primer and 18 μL DPEC water were mixed well. 10 μL of sample in every round was taken for fluorescence in microplate by BioTek. The round number with highest fluorescence signal was selected to amplify the remaining products.

(5) Separation and purification: Mix the PCR product obtained in step (4) with 800 μL of Promega beads, shake the plate for 1 h and remove the supernatant. Then 25 μL of 50 mM NaOH is added to vortex for 5 min. The double strands attached to the magnetic beads were dissociated, the supernatant was aspirated and sequentially added with 12.5 μL of 100 mM HCl, 25 μL of H₂O, 62.5 μL of 2×PBSM, and the resulting solution was used as a secondary library for the next round of screening. The content is about 40 pmol.

(6) The second round of screening: The library was pumped into the negative channel at a flow rate of 2.5 μL/min, and reacted at room temperature for 50 min. Then the pump was used to input the library into the positive channel at a flow rate of 2.5 μL/min. The reaction was carried out at room temperature for 50 min. Then 150 μL of 1×PBS buffer solution is passed at a flow rate of 15 μL/min to remove unreacted chains in the positive channel. The PDMS layer is gently torn off and Luxscan-10K/A microarray scanner is used to scan the chip. Finally, the protein-bound chain was eluted by heating with non-nuclear water at 95° C. for 5 min, and the resulting solution was dried at 60° C. to a volume of 92 μL, which was left for PCR amplification;

(7) Repeat steps (4), (5), (6) to the eighth round of screening;

(8) The fifth, sixth and seventh rounds of PCR amplification products are sent to Shanghai Biotech for sequencing. 120 rounds of sequencing are randomly selected in each round, and the obtained chains are analyzed by IDT software for secondary structure analysis. The optimal aptamers are obtained.

Example 14: Screening of β-Lactoglobulin Aptamers

The specific steps of the β-lactoglobulin aptamer screening include detailed processes such as chip preparation, positive and negative screening process, and PCR amplification, as described below, wherein:

Library:
(SEQ ID NO: 66)
5'-TAMRA-GACAGGCAGGACACCGTAAC-N40-CTGCTACCTCCCTCCTCTTC-3'

TARMA modified forward primer:
(SEQ ID NO: 3)
5'-TARMA-GACAGGCAGGACACCGTAAC-3'

Biotinylated backward primer:
(SEQ ID NO: 4)
5'Biotin-GAAGAGGAGGGAGGTAGCAG-3'

(1) Chip preparation: The microfluidic channel template was fabricated by the combination of lithography mask and chemical etching, and was reserved for the subsequent PDMS channel preparation. The PDMS prepolymer and the curing agent are mixed at a mass ratio of 10:1. After vacuuming, it was poured onto a microfluidic channel template to obtain a PDMS microfluidic channel. A spotting instrument was used to prepare a 5 mg/mL of β-lactoglobulin and a negative protein microarray on a glass substrate. PDMS and the spotted glass substrate are simultaneously plasma treated, and then closely adhered together as a screening chip for the next round of screening.

(2) Screening preparation: The screening chip obtained in step (1) was placed in a constant temperature water bath for incubation for 2 h at 37° C. Then 20 mg/ml of BSA and 0.01 mM of random sequence short-chain ssDNA (20 nt) were introduced and incubated at 37° C. for 1 h. Then, 150 μL of 1×PBST solution was used to clean the positive and negative screen channels.

(3) First round of screening: 0.5 nmol, 125 μL of the original library was heated at 95° C. for 5 min, and immediately frozen on ice for 10 s. Then the syringe was used to deliver the library into the positive channel at a flow rate of 2.5 μL/min. The reaction was carried out at room temperature for 50 min. Then 150 μL of 1×PBS buffer solution was passed at a flow rate of 15 μL/min to remove the unbound ssDNA sequence in the positive channel. The PDMS layer was gently torn off and Luxscan-10K/A microarray scanner is used to scan the chip. Finally, the β-lactoglobulin-bound ssDNA sequence is eluted with DPEC water at 95° C. for 5 min, and the resulting solution is dried to a volume of 92 μL under high purity nitrogen at 50° C.

(4) PCR amplification process: the solution obtained in step (3) is divided into 4 parts of the same solution with a volume of 23 μL. Each step is added with 25 μL of 2×Taq polymerase, 1 μL of 20 μM TAMRA labeled forward primers and 1 μL of 20 μM biotinylated backward primers and the mixture were PCR-amplified. PCR thermal cycling is as follows: 94° C. for 5 min, cycling 94° C. for 30 s, 60.5° C. for 30 s, 72° C. 30 s for 10 rounds and terminated at 72° C. for 5 min. The product obtained in this step is diluted 10 times and then amplified as a template: 5 μL of the diluted PCR product and 1 μL of 2×SYBR Premix Ex Taq™ enzyme, 1 μL of 20 μM TAMRA-labeled forward primer, 1 μL of 20 μM biotinylated backward primer and 18 μL DPEC water were mixed well. 10 μL of sample in every round was taken for fluorescence in microplate by BioTek. The round number with highest fluorescence signal was selected to amplify the remaining products.

(5) Separation and purification: Mix the PCR product obtained in step (4) with 800 μL of Promega beads, shake the plate for 1 h and remove the supernatant. Then 25 μL of 50 mM NaOH is added to vortex for 5 min. The double strands attached to the magnetic beads were dissociated, the supernatant was aspirated and sequentially added with 12.5 μL of 100 mM HCl, 25 μL of H$_2$O, 62.5 μL of 2×PBSM, and the resulting solution was used as a secondary library for the next round of screening. The content is about 40 pmol.

(6) The second round of screening: The library was pumped into the negative channel at a flow rate of 2.5 μL/min, and reacted at room temperature for 50 min. Then the pump was used to input the library into the positive channel at a flow rate of 2.5 μL/min. The reaction was carried out at room temperature for 50 min. Then 150 μL of 1×PBS buffer solution is passed at a flow rate of 15 μL/min to remove unreacted chains in the positive channel. The PDMS layer is gently torn off and Luxscan-10K/A microarray scanner is used to scan the chip. Finally, the protein-bound chain was eluted by heating with non-nuclear water at 95° C. for 5 min, and the resulting solution was dried at 60° C. to a volume of 92 μL, which was left for PCR amplification;

(7) Repeat steps (4), (5), (6) to the eighth round of screening;

(8) The fifth, sixth and seventh rounds of PCR amplification products are sent to Shanghai Biotech for sequencing. 120 rounds of sequencing are randomly selected in each round, and the obtained chains are analyzed by IDT software for secondary structure analysis. The optimal aptamers are obtained.

What is claimed is:

1. A lactoferrin-bound aptamer, wherein the lactoferrin-bound aptamer is a polynucleotide having the nucleotide sequence shown as SEQ ID No: 6.

2. A method for detecting lactoferrin content comprising a step for determining the amount of an aptamer that interacted with the lactoferrin, wherein the aptamer is a polynucleotide having the nucleotide sequence shown as SEQ ID NO: 6.

* * * * *